(12) United States Patent
Nozaki et al.

(10) Patent No.: US 7,279,613 B2
(45) Date of Patent: Oct. 9, 2007

(54) SANITARY NAPKIN

(75) Inventors: Satoshi Nozaki, Kagawa (JP); Wataru Yoshimasa, Kagawa (JP); Kazuya Nishitani, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 313 days.

(21) Appl. No.: 10/179,321

(22) Filed: Jun. 24, 2002

(65) Prior Publication Data
US 2003/0018314 A1 Jan. 23, 2003

(30) Foreign Application Priority Data
Jun. 29, 2001 (JP) ............................. 2001-199325

(51) Int. Cl.
*A61F 13/15* (2006.01)
(52) U.S. Cl. .............................. 604/380; 604/385.101; 604/379; 604/385.16
(58) Field of Classification Search ................ 604/379, 604/380, 385.101, 385.16, 385.17
See application file for complete search history.

(56) References Cited

U.S. PATENT DOCUMENTS

| | | | | | |
|---|---|---|---|---|---|
| 5,057,096 | A | * | 10/1991 | Faglione | 604/385.17 |
| 5,624,423 | A | * | 4/1997 | Anjur et al. | 604/385.21 |
| 5,702,380 | A | * | 12/1997 | Walker | 604/385.17 |
| 5,746,729 | A | * | 5/1998 | Wada et al. | 604/378 |
| 5,807,365 | A | * | 9/1998 | Luceri | 604/367 |
| 5,833,680 | A | * | 11/1998 | Hartman | 604/385.17 |
| 6,350,257 | B1 | * | 2/2002 | Bjorklund et al. | 604/385.01 |
| 6,616,644 | B1 | * | 9/2003 | Mizutani | 604/385.04 |
| 2001/0020157 | A1 | * | 9/2001 | Mizutani et al. | 604/385.04 |

FOREIGN PATENT DOCUMENTS

| | | | |
|---|---|---|---|
| EP | 0880955 A2 | * | 2/1998 |
| EP | 1 097 685 A2 | | 5/2001 |
| JP | 02-144059 | | 6/1990 |
| JP | 07-012120 | | 1/1995 |
| JP | 11-004851 | | 1/1999 |
| JP | 2000-189456 | | 7/2000 |
| WO | WO-96/34589 A2 | | 11/1996 |

OTHER PUBLICATIONS

Japanese Office Action dated Nov. 24, 2006 issued for corresponding Japanese Patent Application 2001-199325.
English Translation of Japanese Office Action dated Nov. 24, 2006 issued for corresponding Japanese Patent Application 2001-199325.

* cited by examiner

*Primary Examiner*—Tatyana Zalukaeva
*Assistant Examiner*—C. Lynne Anderson
(74) *Attorney, Agent, or Firm*—Darby & Darby

(57) ABSTRACT

Disclosed is a sanitary napkin including: a backsheet; a liquid-permeable topsheet; and an absorbent layer which is capable of absorbing a liquid and disposed between the backsheet and the topsheet. At least a part of a region in which the absorbent layer is provided is adapted to receive a liquid. The liquid-receiving region includes a raised region in which a hydrophilic material layer is provided. The raised region is continuously elongated in a longitudinal direction of the sanitary napkin. The raised region includes a front region for coming into contact with a vaginal opening of a wearer and a rear region for coming into contact with buttocks of the wearer. When the front region and the rear region are respectively depressed with a given pressure, an amount of the depression of the rear region is larger than an amount of the depression of the front region.

21 Claims, 5 Drawing Sheets

SANITARY NAPKIN

BACKGROUND OF THE INVENTION

1. Field of the Invention

The present invention relates to a sanitary napkin which is superior in body fit, and highly effective in preventing leakage of a menstrual blood toward buttocks.

2. Description of the Related Art

When a female during menstruation lies down to sleep while wearing a sanitary napkin, there is the possibility of rearward leakage of the menstrual blood along the gluteal fold of the wearer. Particularly when the wearer lies on her back, the menstrual blood is liable to flow rearwardly along the gluteal fold by gravity, causing the rearward leakage.

As sanitary napkins taking measures to prevent such rearward leakage of the menstrual blood in bed, there have been known ones of which a rear portion can readily fit in the gluteal fold.

For example, Patent Gazette of Japanese Patent No. 2784016 discloses an absorbent article to be used as a sanitary napkin, in which an elastic member disposed in a rear part of a liquid-receiving region is made flexible to fit in the gluteal fold.

On the other hand, Japanese Unexamined Patent Publication No. 2000-189456 discloses an absorbent article to be used as a sanitary napkin, in which an absorbent layer having a first raised portion and a second raised portion. In this absorbent article, the first raised portion is aimed at coming into close contact with a discharging part of the wearer's body, and the second raised portion is aimed at fitting in the gluteal fold. Between the first and second raised portions, in addition, there is provided a flexible region having a stiffness lower than those of the two raised portions, thereby enabling the absorbent article to deform so that the first and second raised portions may fit on the body.

However, in the absorbent article disclosed in Patent Gazette of Japanese Patent No. 2784016, only the measure to make the elastic member of the rear part fit in the gluteal fold is taken, but no measure is taken for fit of the absorbent article against the vaginal opening and its surroundings. Therefore, when the wearer lies on her back in bed, the menstrual blood discharged from the vaginal opening is liable to migrate to the wearer's back directly along the gluteal fold. However, since the gluteal fold extending rearwardly from the anus is so deep, if the menstrual blood flowing rearwardly from the vaginal opening is collected in the fold, it is impossible to certainly prevent the rearward leakage of the menstrual blood only with the measure using the elastic member of the rear part.

In the absorbent article disclosed in Japanese Unexamined Patent Publication No. 2000-189456, on the other hand, the amount of menstrual blood flowing rearwardly in bed can be reduced. by bringing the first raised portion placed forward into close contact with the discharging part. However, since the flexible region is provided between the first and second raised portions, the absorbent article is liable to bend at the flexible region when the wearer's body moves in bed. As a result, the first and second raised portions may possibly move away from the wearer's body or slip off the discharging part and the gluteal fold. In addition, since the flexible region is liable to move away from the wearer's body, a menstrual blood which could not dammed up by the first raised portion may possibly leak sidewardly at the flexible region.

SUMMARY OF THE INVENTION

The present invention has been worked out in view of the shortcoming in the prior art set forth above. It is therefore an object of the present invention to provide a sanitary napkin which enables a liquid-receiving region to readily come into close contact with the vaginal opening and its surroundings and also with the gluteal fold, thereby effectively preventing rearward leakage of a menstrual blood.

According to the present invention, there is provided a sanitary napkin comprising:

a backsheet;

a liquid-permeable topsheet; and an absorbent layer which is capable of absorbing a liquid and disposed between the backsheet and the topsheet, at least a part of a region in which the absorbent layer is provided being adapted to receive a liquid, wherein the liquid-receiving region includes a raised region in which a hydrophilic material layer is provided, the raised region being continuously elongated in a longitudinal direction of the sanitary napkin, the raised region including a front region for coming into contact with a vaginal opening of a wearer and a rear region for coming into contact with buttocks of the wearer, and wherein when the front region and the rear region are respectively depressed with a given pressure, an amount of the depression of the rear region is larger than an amount of the depression of the front region.

It should be noted that the hydrophilic material layer may be provided either between the topsheet and the absorbent layer or on the topsheet.

In the present invention, since the liquid-receiving region is provided with the longitudinally elongated raised region, the raised region comes into contact with an area from the vaginal opening, through the anus, to the gluteal fold. Therefore, a menstrual liquid discharged from the vaginal opening can be absorbed by the raised region in the vicinity of the vaginal opening and introduced into the absorbent layer. If a part of the menstrual blood can not be absorbed in the vicinity of the vaginal opening, such liquid, which would otherwise flow rearwardly along the gluteal fold, will be effectively collected by the elongated raised region. Particularly because the rear region of the raised region is constructed to be more deformable than the front region, the rear region of the raised region can readily enter the gluteal fold, so that the menstrual liquid tending to flow along the gluteal fold can be effectively collected by the rear region of the raised region.

With the elongated raised region being provided, moreover, the sanitary napkin can be increased in stiffness at a part for covering the area from the vaginal opening to the buttocks. Therefore, it is possible to prevent undesirable folding or twisting of the sanitary napkin at the part for covering the area from the vaginal opening to the buttocks, thereby maintaining close contact between the raised region and the wearer's body constantly.

For example, when the front region and the rear region are in a dry state and are respectively depressed with a pressure of 3.43 kPa, the amount of the depression of the front region is preferably at least 3 mm and the amount of the depression of the rear region is preferably at least 5 mm. When the amount of the depression resulted from a given pressure is made larger in the rear region and the amounts of the depressions are set within the foregoing ranges, the rear region of the raised region can readily deform to enter the gluteal fold. On the other hand, although the amount of the depression of the front region is smaller than that of the rear region and the stiffness of the front region is slightly higher than that of the rear region, since the vaginal opening and its surroundings are relatively flat as compared with the buttocks, the front region comes into close contact with the vaginal opening and its surroundings sufficiently by setting the amount of the depression of the front region within the foregoing range. In addition, since the fiber density of the front region is increased by increasing the stiffness of the front region, the absorption speed of the menstrual blood becomes faster in the front region due to capillary action between fibers, thereby decreasing an amount of the menstrual blood tending to flow rearwardly along the raised region.

When an artificial body fluid is applied onto the front region and the rear region at the same amount and feed rate, therefore, it is preferred that an absorption speed of the artificial body fluid in the front region is faster than that in the rear region.

For example, when 3 cc of artificial body fluid is applied at a feed rate of 90 cc/minute, a difference in the absorption speed of the artificial body fluid between the front region and the rear region is preferably in a range of 10 to 15 seconds. Also preferably, the absorption speed in the front region is equal to or less than 10 seconds, and the absorption speed in the rear region is equal to or less than 60 minutes. With the absorption speeds of the menstrual blood being set within the foregoing ranges, the menstrual blood can be effectively absorbed by the front region of the raised region, and in the rear region which can readily fit in the gluteal fold, the effect of preventing rearward leakage of the menstrual blood can be improved.

In one embodiment, a height from a peripheral region of the liquid-receiving region outside of the raised region to a surface of the rear region may be larger than a height from the peripheral region to a surface of the front region. With the rear region being made higher, the rear region can readily enter the gluteal fold, thereby preventing the rearward leakage of the menstrual blood along the gluteal fold.

In this case, the height from the peripheral region to the surface of the rear region is preferably at most 1.5 times the height from the peripheral region to the surface of the front region. With the heights being thus set, an uncomfortable feeling is hardly caused when the rear region enters the gluteal fold.

However, it is also possible that the height from the peripheral region to the surface of the front region is equal to the height from the peripheral region to the surface of the rear region.

Preferably, both the height from the peripheral region to the surface of the front region and the height from the peripheral region to the surface of the rear region are in a range of 5 to 20 mm. Within the foregoing range, the surface of the raised region hardly moves away the vaginal opening, anus, and gluteal fold when the sanitary napkin is attached to an inner side of a crotch portion of an undergarment.

Preferably, the front region and the rear region of the raised region are identical in width, and a width of the raised region as measured at ½ of a height from a peripheral region of the liquid-receiving region outside of the raised region to a surface of the raised region is in a range of 5 to 80 mm. Within the foregoing range, the raised region can closely contact the vaginal opening, anus, and gluteal fold and hardly causes an uncomfortable feeling during motion of the wearer's body.

When the respective front and rear regions are applied 10 cc of artificial body fluid at a feed rate of 10 cc/minute, allowed to stand for one minute after application of the artificial body fluid, and then applied a pressure of 3.43 kPa for one hour with a plane covering the entire surface of the respective front and rear regions, bulk recovery percentages of the respective front and rear regions one minute later after removal of the pressure are preferably equal to or more than 50%. With the recovery percentages from compression being set within the foregoing range, when the raised region is given a menstrual blood to be in a wet state, the front region can readily deform to conform to the uneven configuration around the vaginal opening, and the rear region can readily enter to enter the gluteal fold.

When the sanitary napkin is in a dry state, a stiffness as measured by clamping front and rear ends of the raised region with a taper stiffness tester is preferably in a range of 0.5 to 4.0 mN·m. When the sanitary napkin is in a dry state, moreover, a stiffness of the front region alone as measured with the taper stiffness tester is preferably more than 1.0 times and less than or equal to 2.0 times a stiffness of the rear region alone as measured with the taper stiffness tester. With the stiffness of the raised region being set within the foregoing ranges, the raised region can deform to conform to the wearer's body while being prevented from moving away from the wearer's body during wear.

Preferably, the sanitary napkin further comprises leakage preventing walls disposed on both sides of the raised region and extending longitudinally of the sanitary napkin, and rear ends of the leakage preventing walls are positioned closer to a rear end of the sanitary napkin than a rear end of the raised region. With such construction, if a menstrual blood should leak rearwardly from the rear end of the raised region, sideward leakage of the menstrual blood can be prevented by the leakage preventing walls disposed on both sides.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

Figure 1:
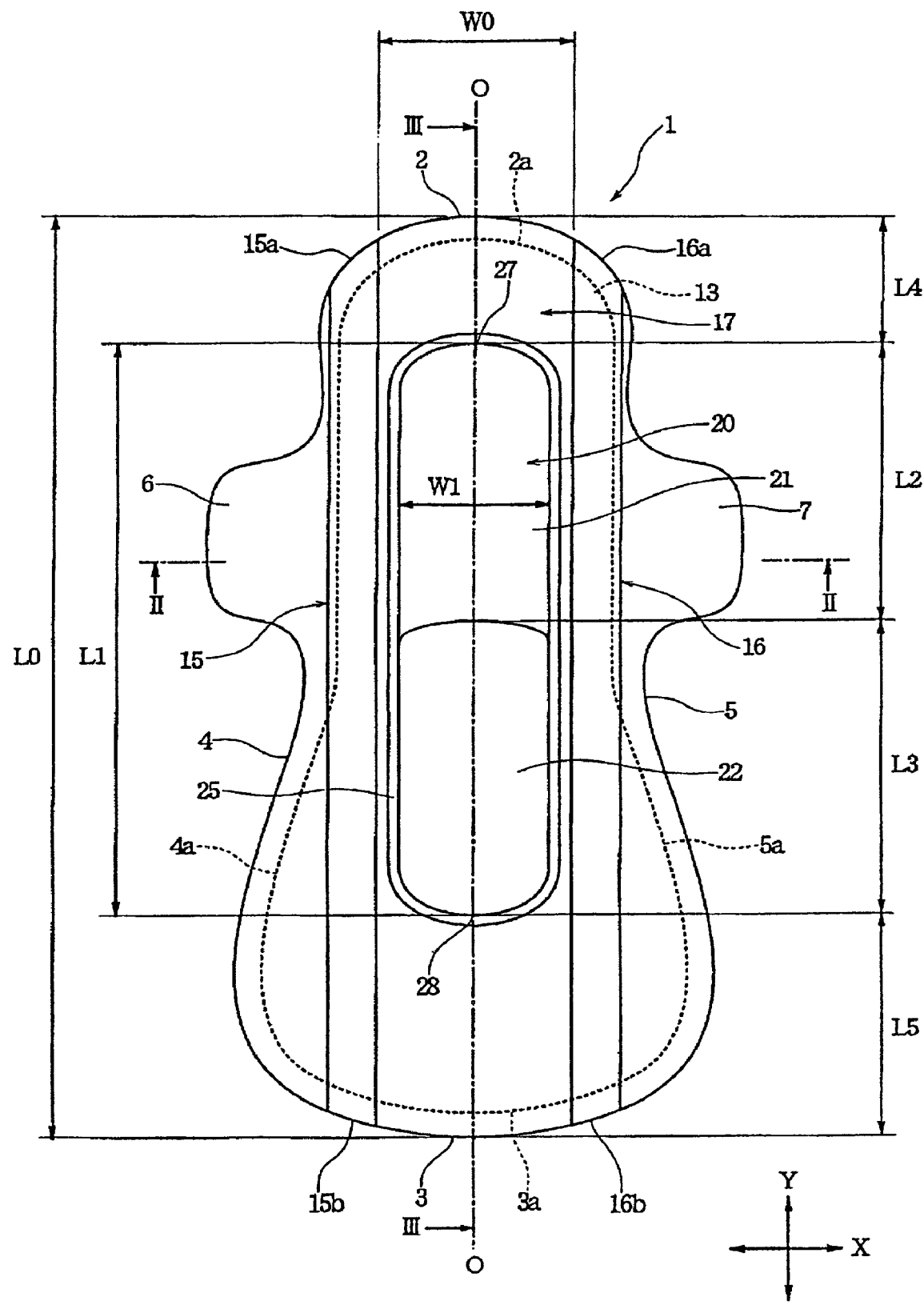
FIG. 1 is a top plan view showing a sanitary napkin according to a first embodiment of the present invention.
Figure 2:
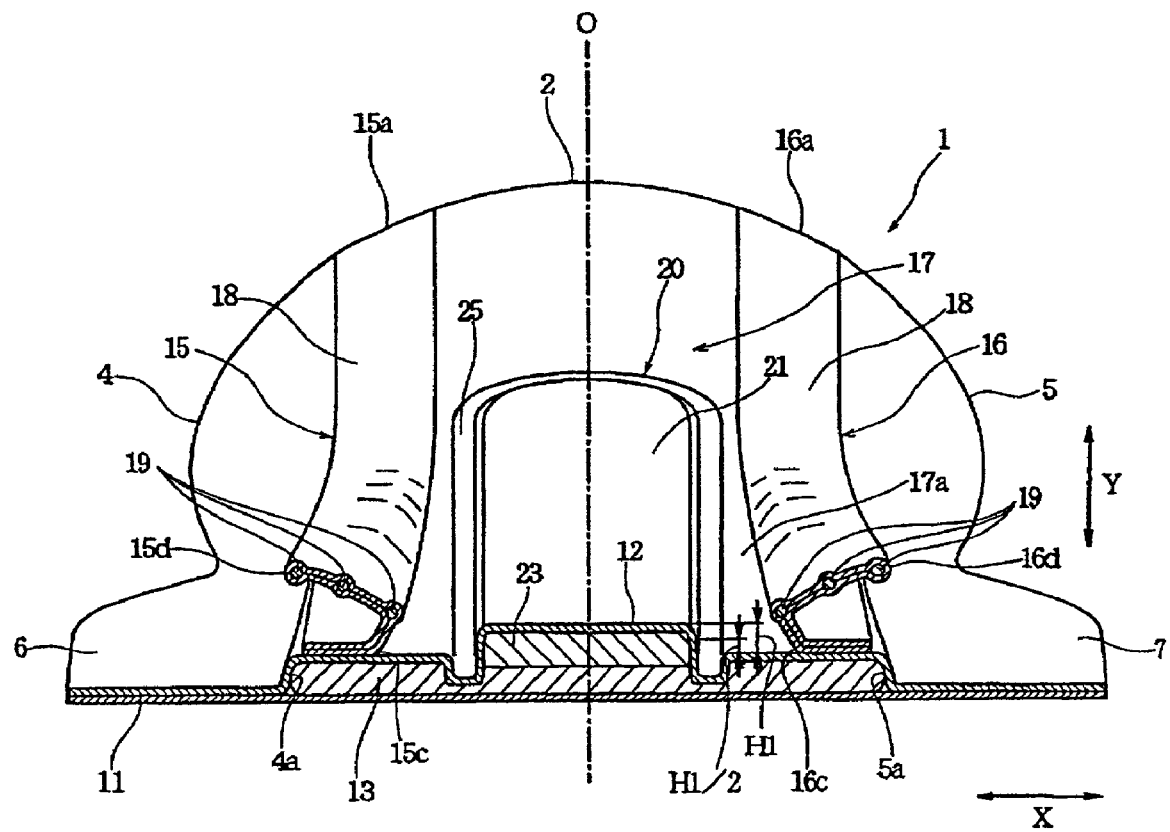
FIG. 2 is a cross-sectional view taken along line II-II of FIG. 1.

FIG. 1 is a top plan view showing a sanitary napkin 1 according to a first embodiment of the present invention; FIG. 2 is a sectional view of the sanitary napkin 1 as taken along line II-II of FIG. 1; and FIG. 3 is another sectional view of the sanitary napkin 1 as taken along line III-III of FIG. 1, in which the sanitary napkin 1 is cut along a longitudinally extending centerline O.

Figure 3:
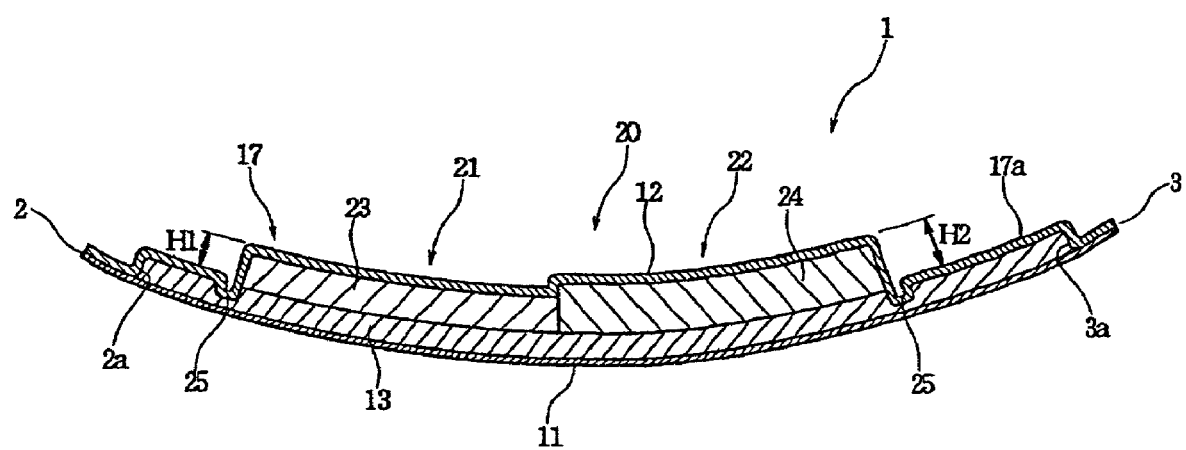
FIG. 3 is a longitudinal sectional view taken along line III-III of FIG. 1.

The sanitary napkin 1 shown in FIGS. 1 to 3 is to be worn by a female during menstruation while being attached to an inner side of a crotch portion of an undergarment. The shown sanitary napkin 1 is particularly suitable for use while sleeping.

As seen from the top plan view of FIG. 1, the sanitary napkin 1 has a generally arcuate front edge 2 and a rear edge 3 which is also arcuate, and the rear edge 3 extends longer in the width direction (X-direction) than the front edge 2. Left-hand and right-hand side edges 4 and 5 are curved such that the distance between the left-hand side edge 4 and the right-hand side edge 5 (i.e., the width of the sanitary napkin 1) is larger on the side close to the rear edge 3, which will be brought into contact mainly with a crotch of a wearer during use, than on the side close to the front edge 2, which will be brought into contact mainly with buttocks of a wearer during use.

In a position offset toward the front edge 2 from a laterally extending centerline of the sanitary napkin 1, the left-hand side edge 4 and the right-hand side edge 5 are respectively bulged outwardly in the width direction (X-direction). These portions thus bulged are wing portions 6 and 7.

As shown in the sectional views of FIGS. 2 and 3, the sanitary napkin comprises a liquid-impermeable backsheet 11 and a liquid-permeable topsheet 12. The backsheet 11 and the topsheet 12 are of the shape identical to that of the sanitary napkin 1, i.e., of the shape having the front edge 2, rear edge 3, left-hand side edge 4 and right-hand side edge 5 to provide the wing portions 6 and 7.

As shown in FIGS. 2 and 3, an absorbent layer 13 is provided on the backsheet 11. The absorbent layer 13 is of a given thickness, and has a front edge 2a, a rear edge 3a, a left-hand side edge 4a and a right-hand side edge 5a, as shown in broken line in FIG. 1. The front edge 2a and the rear edge 3a of the absorbent layer 13 are spaced inwardly apart from the front edge 2 and the rear edge 3 of the sanitary napkin 1 by 3 to 10 mm, respectively. Therefore, the front edge 2a and the rear edge 3a are similar in shape to the front edge 2 and the rear edge 3, respectively. The left-hand side edge 4a and the right-hand side edge 5a of the absorbent layer 13 are similar in shape to the left-hand side edge 4 and the right-hand side edge 5 of the sanitary napkin 1, except for the edge portions of the wing portions 6 and 7, and spaced inwardly apart from the left-hand side edge 4 and the right-hand side edge 5 by 3 to 10 mm, respectively. In a region outside of the front edge 2a, the rear edge 3a, the left-hand side edge 4a and the right-hand side edge 5a of the absorbent layer 13, the backsheet 11 and the topsheet 12 are bonded to each other through a hot-melt adhesive or the like.

On the surface of the topsheet 12, there are provided a pair of leakage preventing walls 15 and 16, which are equally spaced from the longitudinally extending centerline O toward the left-hand and right-hand side edges 4 and 5. In the sanitary napkin 1, a region, which has a width W0 between the leakage preventing walls 15 and 16 and in which the absorbent layer 13 is present, is a liquid-receiving region 17.

In the liquid-receiving region 17, there is provided a raised region 20 which is elongated longitudinally of the sanitary napkin 1. The raised region 20 has a length L1 and a width W1. The raised region 20 includes a front region 21 of a length L2 and a rear region 22 of a length L3. As shown in FIG. 3, when a region of the liquid-receiving region 17 outside of the raised region 20 is designated a peripheral region 17a, the height from the peripheral region 17a to the surface of the front region 21 is indicated by H1, and the height form the peripheral region 17a to the surface of the rear region 22 is indicated by H2.

Here, when the periphery of the raised region 20 is taken as a starting point for measurement of the lengths L1, L2 and L3 and the width W1, these dimensions are measured at a height of ½ of the height H1 or H2, as shown in FIG. 2.

In the raised region 20, as shown in FIG. 3, the front region 21 has a first hydrophilic material layer 23 disposed between the absorbent layer 13 and the topsheet 12; and the rear region 22 has a second hydrophilic material layer 24 disposed between the absorbent layer 13 and the topsheet 12. The first and second hydrophilic material layers 23 and 24 function as cushion layers, because they can be depressed more than the absorbent layer 13 upon compression and are also higher in recovery percentage from compression than the absorbent layer 13.

At the boundary between the raised region 20 and the peripheral region 17a, a compressed groove 25 is formed to surround the raised region 20. In the compressed groove 25, the topsheet 12 and the absorbent layer 13 are heated under pressure, so that the absorbent layer 13 is crushed and the topsheet 12 is recessed to conform to the surface of the crushed portion.

The individual leakage preventing walls 15 and 16 are composed of a strip-shaped hydrophobic sheet 18 folded in two and a plurality of elastic members 19 disposed and bonded therebetween. The hydrophobic sheet 18 and the elastic members 19 extend longitudinally of the sanitary napkin 1. In an intermediate position of the sanitary napkin 1 in the longitudinal direction thereof, the hydrophobic sheets 18 thus folded in two are partly joined to the surface of the topsheet 12 to have longitudinally extending root ends 15c and 16c, from which the leakage preventing walls 15 and 16 start to rise. Portions including the fold lines of the hydrophobic sheets 18 form free ends 15d and 16d of the leakage preventing walls 15 and 16.

In front and rear positions of the sanitary napkin 1, on the other hand, the hydrophobic sheets 18 are bonded to the surface of the topsheet 12 while being folded in two to be flat. Here, the elastic members 19 are bonded to the hydrophobic sheets 18 while being longitudinally stretched. Therefore, the sanitary napkin 1 is curved due to an elastic contractive force of the elastic members 19, resulting in that the leakage preventing walls 15 and 16 are raised up in the intermediate position of the sanitary napkin 1 in the longitudinal direction thereof with their free ends 15d and 16d being spaced apart from the topsheet 12.

The backsheet 11 is formed of a liquid-impermeable and moisture-permeable (breathable) resin film, a nonwoven fabric, a laminate of the resin film and the nonwoven fabric, or the like. The absorbent layer 13 is formed of a mixture of crushed pulp and SAP (superabsorbent polymer) wrapped in liquid-permeable paper, air-laid pulp formed into a sheet by processing it with a binder, polymer sheet, absorbent paper, cotton linter pulp, or the like.

As set forth above, the first and second hydrophilic material layers 23 and 24 have a cushioning property, and may be formed of a hydrophilic material of a three-dimensional framework capable of passing a liquid into the absorbent layer 13, as exemplified by a foamed resin having open-cells therein, which is made of a resin material such as polyurethane, polyethylene or polyvinyl alcohol.

In an alternative, the first and second hydrophilic material layers 23 and 24 may be formed of a through-air bonded nonwoven fabric in which heat-fusible synthetic fibers treated to be hydrophilic are fusion-bonded to each other with heated air. In this case, the synthetic fibers are selected from PE (polyethylene) fibers, PET (polyethylene terephthalate) fibers, bicomponent synthetic fibers of PE and PP (polypropylene), or bicomponent synthetic fibers of PE and PET. In another alternative, also usable is a laminate of a nonwoven fabric in which hydrophilic fibers, such as rayon, and/or synthetic fibers treated to be hydrophilic are entangled about each other by needle punching and a spunbonded nonwoven fabric of the synthetic fibers. In still another alternative, use can be made of a fibrous web in which synthetic fibers treated to be hydrophilic and/or the hydrophilic fibers are accumulated without bonding.

Between the first and second hydrophilic material layers 23 and 24, the first hydrophilic material layer 23 has a higher density. Therefore, the second hydrophilic material layer 24 can be depressed more than the first hydrophilic material layer 23 upon compression and is also higher in recovery percentage from compression than the first hydrophilic material layer 23. On the other hand, the absorbent layer 13 has a higher density than the first and second hydrophilic material layers 23 and 24. Therefore, it cannot be depressed as much as the hydrophilic material layers 23 and 24 upon compression and is also lower in recovery percentage from compression than the hydrophilic material layers 23 and 24.

The topsheet 12 is liquid-permeable, as exemplified by a nonwoven fabric formed of hydrophilic fibers or synthetic fibers treated to be hydrophilic or an apertured nonwoven fabric. In an alternative, the topsheet 12 may be formed of a polyolefin resin film having a large number of apertures formed therein, the surface of which is treated to be hydrophilic.

The topsheet 12 is preferably stretchable and expandable along its plane. In order to provide the topsheet 12 with such nature, preferred are the apertured resin film, a reticulated resin film, a stretchable nonwoven fabric, an embossed nonwoven fabric, an embossed resin film, and the like. If the topsheet 12 can be stretched in a range of 110% to 150% along its plane, when the front region 21 and the rear region 22 of the raised region 20 are pressed against the wearer's skin, the topsheet 12 can be flexibly deformed together with the first and second hydrophilic material layers 23 and 24 functioning as the cushion layers, so that the front region 21 and the rear region 22 can readily deform and conform to the uneven configuration of the wearer's body.

On the exterior surface of the backsheet 11, on the other hand, first and second pressure sensitive adhesive layers (not shown) are formed. The first pressure sensitive adhesive layer is positioned in a region along the centerline O; and the second pressure sensitive adhesive layer is positioned in the wing portions 6 and 7.

Upon use, the sanitary napkin 1 is attached to an undergarment such that its body portion is fixed on the inner side of the crotch portion of the undergarment through the first pressure sensitive adhesive layer, and the wing portions 6 and 7 are folded at the side edges of the crotch portion toward the outer side of the crotch portion and then fixed thereon through the second pressure sensitive adhesive layer.

When the sanitary napkin 1 is worn by the wearer, the liquid-receiving region 17 is brought into close contact with the wearer's body while being deformed and concavely curved. Here, the raised region 20 comes into close contact with an area from the vaginal opening and labia, through the perineum and anus, to the gluteal fold. At this time, the front region 21 of the raised region 20 comes into close contact with the vaginal opening and labia and their surroundings; and the rear region 22 fits in the gluteal fold. Since the front region 21 of the raised region 20 is provided with the first hydrophilic material layer 23 having a cushioning property, the front region 21 can be deformed to conform to the uneven configuration of the vaginal opening and labia for close contact.

The rear region 22 can be depressed more than the front region 21 upon compression, and is higher in recovery percentage from compression than the front region 21. Therefore, the rear region 22 can be deformed to flexibly conform to the deep gluteal fold, resulting in close contact between the rear region 22 and the gluteal fold. On the other hand, although the front region 21 cannot be depressed as much as the rear region 22 upon compression, it is still permitted to deform to conform to the relatively moderately uneven configuration of the vaginal opening and labia and their surroundings, thereby assuring close contact between the front region 21 and the vaginal opening and labia and their surroundings.

In addition, since the raised region 20 is elongated in the longitudinal direction of the sanitary napkin 1, the sanitary napkin 1 has a relatively higher stiffness over the entire raised region 20. Since the raised region 20 having such relatively higher stiffness comes into contact with the wearer's body from the vaginal opening and its surroundings to the gluteal fold, the sanitary napkin 1 is prevented from being folded in v shape or twisted in a position between the vaginal opening and the gluteal fold. Therefore, the liquid-receiving region 17 including the raised region 20 hardly comes off of the wearer's body, assuring close contact from the vaginal opening to the gluteal fold.

In a condition where the wearer lies on her back, a menstrual blood discharged from the vaginal opening is received by the front region 21 of the raised region 20. Since the front region 21 has the first hydrophilic material layer 23 of a high density, the menstrual blood is rapidly absorbed due to capillary action of the hydrophilic material layer 23, and given to and retained by the absorbent layer 13. Here, a part of the menstrual blood may possibly flow farther rearwardly by gravity. In this case, if such menstrual blood flows along the raised region 20, it will be absorbed by the absorbent layer 13 as flowing along the raised region 20. If such menstrual blood reaches the deep gluteal fold, it will be dammed up by the rear region 22 of the raised region 20 in close contact with the gluteal fold. If such menstrual blood flows out rearwardly of the rear end of the raised region 20, it will be absorbed by the absorbent layer 13 in the liquid-receiving region 17 in a position behind the raised region. On the other hand, a menstrual blood tending to leak in the width direction is dammed up by the leakage preventing walls 15 and 16 positioned on two sides of the liquid-receiving region 17, thereby preventing sideward leakage of the menstrual blood.

The sanitary napkin 1 suitable for use while sleeping has an entire length L0 of 200 to 350 mm from the front edge 2 to the rear edge 3. The length L1 of the raised region 20 from the front end 27 to the rear end 28 is preferably in a range of 70 to 300 mm. Below 70 mm, it is impossible to bring the rear region 22 into contact with the perineum or anus while keeping the front region 21 in contact with the vaginal opening or its surroundings. In order to assure close contact between the rear region 22 and the gluteal fold, the length L1 is preferably at least 150 mm. If the length L1 is in excess of 300 mm, the rear end 28 comes into contact with the wearer's body beyond the coccyx, so that the wearer is liable to feel a foreign body sensation. In order to prevent occurrence of such foreign body sensation, the length L1 is more preferably at most 280 mm.

On the other hand, a ratio of the length L2 of the front region 21 to the length L3 of the rear region 22 in the raised region 20 is preferably 40-70%:60-30%. In addition, the length L2 of the front region 21 is preferably larger than the length L3 of the rear region 22. Since the first hydrophilic material layer 23 of the front region 21 has a liquid absorption speed faster than that of the second hydrophilic material layer 24 of the rear region 22, the possibility of absorbing a menstrual blood, which tends to flow toward the buttocks, by the raised region 20 can be increased by setting the length L2 of the front region 21 larger.

It is preferred that the width W1 of the raised region 20 is constant over the front region 21 and the rear region 22 and the width W1 is in a range of 5 to 80 mm. However, the width of the front region 21 and the width of the rear region 22 may differ from each other within such range. If the width W1 is less than 5 mm, a menstrual blood discharged from the vaginal opening can not be certainly collected by the raised region 20. In order to assure close contact between the front region 21 of the raised region 20 and the vaginal opening and labia and their surroundings, it is more preferred that the width W1 is at least 20 mm. If the width W1 is more than 80 mm, on the other hand, it becomes larger than the width of the crotch of the wearer's body, tending to cause a foreign body sensation. It is more preferred that the width W1 is at most 60 mm.

As shown in FIG. 3, in the sanitary napkin 1 according to the first embodiment, the height H2 from the surface of the peripheral region 17a to the surface of the rear region 22 is larger than the height H1 from the surface of the peripheral region 17a to the surface of the front region 21. In the first hydrophilic material layer 23 of the front region 21, the liquid absorption speed has priority over the flexibility, and in the second hydrophilic material layer 24 of the rear region 22, priority is given to the flexibility. Here, by setting the height H2 of the rear region 22 larger, the flexible rear region 22 can easily fit in the gluteal fold.

Preferably, the height H2 is 1.1 to 1.5 times the height H1. In excess of 1.5 times, when the front region 21 comes into contact with the vaginal opening and its surroundings, the rear region 22 tends to cause a foreign body sensation to the buttocks. On the other hand, both the heights H1 and H2 are preferably in a range of 5 to 20 mm. Below 5 mm, there is a possibility of causing a clearance between the surface of the raised region 20 and the wearer's body in case where the undergarment has a weak biasing force. In excess of 20 mm, the raised region 20 may cause folds or distortion due to pressure upon close contact between the surface of the raised region 20 and the wearer's body, so that a clearance tends to cause between the surface of the raised region 20 and the wearer's body due to the folds or distortion.

In the front region 21 of the raised region 20, priority is given to the liquid absorption speed, and in the rear region 22, priority is given to the flexibility, as set forth above. Preferred values of the flexibility and the liquid absorption speed for the front region 21 and the rear region 22 are as follows.

Hereinbelow, the term "dry" refers to a state where a sanitary napkin is allowed to stand for at least 30 minutes in an environment having a temperature of 20±2° C. and a relative humidity of 65±2%, according to JIS P-8111 "Standard Condition for Moisture Conditioning and Testing."

In the sanitary napkin 1, when the front region 21 and the rear region 22 of the raised region 20 are depressed with a given pressure, the amount of the depression of the rear region 22 is larger than that of the front region 21. That is, the rear region 22 has a larger compressibility than the front region 21.

When a pressure of 3.43 kPa is applied to the front region 21 by placing a flat plate over the entire surface of the front region 21 and then applying a load to the flat plate, the amount of the depression of the front region 21 resulted from the applied pressure is preferably at least 3 mm, more preferably at least 5 mm. When a pressure of 3.43 kPa is likewise applied to the rear region 22, on the other hand, the amount of the depression of the rear region 22 resulted from the applied pressure is preferably at least 5 mm, more preferably at least 10 mm.

By providing a difference in the amount of the depression between the front region 21 and the rear region 22 while setting the individual depression amounts within the foregoing ranges, the front region 21 can be deformed to conform to the uneven configuration of the vaginal opening and its surroundings for assuring close contact, and the rear region 22 can be flexibly deformed to enter the gluteal fold.

It should be noted that the recovery percentage from compression (elastic modulus in compression) in a wet state is also higher in the rear region 22 than in the front region 21.

Here, the term "wet" refers to a state where 10 cc of artificial body fluid containing 10% by weight of glycerin, 1% by weight of carboxymethyl cellulose and the balance being distilled water is applied to the surface of the raised region 20 at a feed rate of 10 cc/minute, and the sanitary napkin is allowed to stand for one minute after application of the artificial body fluid.

The recovery percentage is measured as follows. Firstly, the height H1 of the front region 21 in the wet state is measured. Immediately after that, a load is applied to a flat plate covering the entire surface of the front region 21 for application of a pressure of 3.43 kPa for one hour. Then, one minute later after removal of the pressure, the height H1' of the front region 21 is measured, and the compressive recovery percentage is obtained by (H1'/H1)×100(%). The compressive recovery percentage of the rear region 22 is likewise measured. The compressive recovery percentage is also measured in the dry state.

In the sanitary napkin 1, the compressive recovery percentages of the front region 21 and the rear region 22 in the dry state are preferably at least 60%, more preferably at least 70%. On the other hand, the compressive recovery percentages in the wet state with the foregoing artificial body fluid are preferably at least 50%, more preferably at least 60%.

If the compressive recovery percentages are less than foregoing values, the raised region 20 hardly deforms to conform to the uneven configuration of the wearer's body, and more particularly, the rear region 22 hardly deforms to conform to the configuration of the gluteal fold.

On the other hand, it is preferred that the stiffness of the raised region 20 does not change very much over the entire raised region 20. The stiffness of the raised region 20 in the dry state as measured by clamping the front and rear ends of the raised region 20 of the sanitary napkin 1 with a taper stiffness tester according to JIS P-8125, is preferably in a range of 0.5 to 4.0 mN·m, more preferably in a range of 1.5 to 4.0 mN·m. On the other hand, the stiffnesses of the respective front region 21 and rear region 22 of the raised region 20 of the napkin in the dry state are measured by clamping the front region 21 alone or the rear region 22 alone with the taper stiffness tester. The stiffness of the front region 21 alone is preferably more than 1.0 time and less than or equal to 2.0 times the stiffness of the rear region 22 alone. More preferably, the stiffness of the front region 21 alone is less than or equal to 1.5 times the stiffness of the rear region 22 alone. Here, the stiffness of the front region 21 is preferably in a range of 1.8 to 4.0 mN·m; and the stiffness of the rear region 22 is preferably in a range of 1.5 to 4.0 mN·m.

With the stiffness of the raised region 20 set within the foregoing range and with the difference between the stiffnesses of the front region 21 and rear region 22 set within the foregoing range, the sanitary napkin 1 during wear can be effectively prevented from being folded in V shape at the raised region 20 and spaced away from the wearer's body at the fold.

Next, with respect to the liquid absorption speeds of the respective front region 21 and rear region 22, when 3 cc of artificial body fluid is applied at a feed rate of 90 cc/minute, the absorption speed of the artificial body fluid in the front region 21 is preferably equal to or less than 10 seconds and the absorption speed of the artificial body fluid in the rear region 22 is preferably equal to or less than 60 seconds. It is also preferred that the difference between the absorption speed in the front region 21 and the absorption speed in the rear region 22 is 10 to 50 seconds.

In the case where the absorption speed in the front region 21 is equal to or less than 10 seconds, a menstrual blood discharged from the vaginal opening can be absorbed rapidly by the front region 21 to minimize the menstrual blood flowing to the rear region 22. In the case where the absorption speed in the rear region 22 is equal to or less than 60 seconds and the difference between the absorption speed in the front region 21 and the absorption speed in the rear region 22 is set within the foregoing range, on the other hand, the menstrual blood flowing rearwardly can be dammed up by the rear region 21, thereby minimizing the rearward leakage of the menstrual blood beyond the raised region 20.

Figure 4:
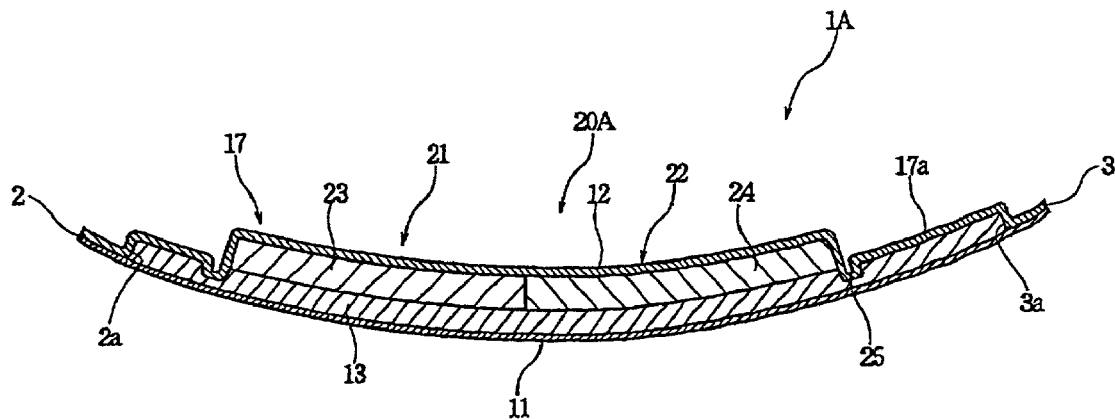
FIG. 4 is a sectional view corresponding to FIG. 3, which shows a sanitary napkin according to a second embodiment of the present invention.
Figure 5:
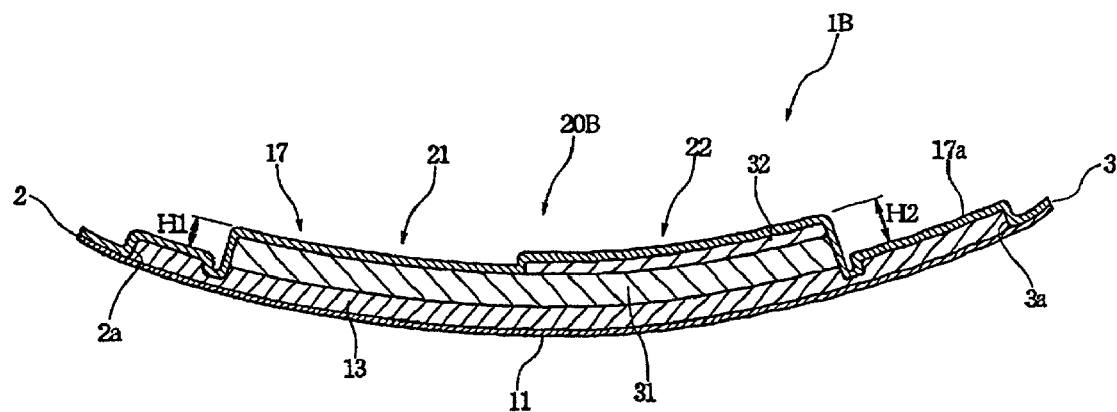
FIG. 5 is a sectional view corresponding to FIG. 3, which shows a sanitary napkin according to a third embodiment of the present invention.

FIGS. 4 and 5 are sectional views respectively showing a sanitary napkin 1A according to a second embodiment of the present invention and a sanitary napkin 1B according to a third embodiment of the present invention, as cut along the centerlines O of the sanitary napkins similar to FIG. 3. Here, the detailed description of the portions having the same constructions as those of the first embodiment shown in FIG. 3 will be omitted by designating them by the common reference numerals.

The sanitary napkin 1A of FIG. 4 according to the second embodiment has a raised region 20A, of which the front region 21 is provided with the first hydrophilic material layer 23 which similar to that of FIG. 3 and the rear region 22 is provided with the second hydrophilic material layer 24 which similar to that of FIG. 3, except that the height from the surface of the peripheral region 17a to the surface of the raised region 20A does not change between the front region 21 and the rear region 22.

The characteristics of the raised region 20A and the front and rear regions 21 and 22 are the same as those of the first embodiment shown in FIG. 3. That is, the liquid absorption speed is faster in the front region 21, and the rear region 22 is flexible so as to deform in conformity with the gluteal fold.

The sanitary napkin 1B of FIG. 5 according to the third embodiment has a raised region 20B, of which a difference in height is provided between the front region 21 and the rear region 22. The optimum values of the height H1 from the surface of the peripheral region 17a to the surface of the front region 21, the height H2 from the surface of the peripheral region 17a to the surface of the rear region 21 and so on are the same as those of the first embodiment shown in FIG. 3.

In the third embodiment, however, the raised region 20B is constructed such that a third hydrophilic material layer 31 is provided to extend over the front region 21 and the rear region 22, and a fourth hydrophilic material layer 32 is disposed on the third hydrophilic material layer 31 within the rear region 22. The third hydrophilic material layer 31 has the same construction as that of the first hydrophilic material layer 23; and the fourth hydrophilic material layer 32 has the same construction as that of the second hydrophilic material layer 24. That is, the fourth hydrophilic material layer 32 is constructed to be flexible so that it may be depressed more upon compression, as compared with the third hydrophilic material layer 31. As a result, the characteristics of the front region 21 and rear region 22 of the raised region 20B shown in FIG. 5 are the same as those of the first embodiment shown in FIG. 3.

In the foregoing embodiments, as the relationship between the raised region 20, 20A or 20B and the leakage preventing walls 15 and 16, rear ends 15b and 16b of the leakage preventing walls 15 and 16 are preferably positioned behind the rear end 28 of the raised region 20, 20A or 20B. More preferably, the rear ends 15b and 16b of the leakage preventing walls 15 and 16 are spaced rearwardly apart from the rear end 28 of the raised region by at least 40 mm.

With such construction, if the menstrual blood should leak rearwardly beyond the rear end 28 of the raised region, the leakage preventing walls can prevent sideward leakage of the menstrual blood.

On the other hand, front ends 15a and 16a of the leakage preventing walls 15 and 16 may be positioned either ahead of or behind the front end 27 of the raised region 20, 20A or 20B, but it is preferred that the front ends 15a and 16a are not spaced rearwardly apart from the front end 27 by 40 mm or more. If the front ends 15a and 16a of the leakage preventing walls 15 and 16 are spaced rearwardly apart from the front end 27 by 40 mm or more, it becomes difficult to prevent the menstrual blood tending to flow rearwardly along the raised region from leaking sidewardly toward the left-hand and right-hand sides.

EXAMPLE

Example

The sanitary napkin 1 of the structure shown in FIGS. 1 to 3 was prepared as follows.

Backsheet 11: Polyethylene film having a basis weight of 25 g/m$^2$.

Topsheet 12: Liquid-permeable nonwoven fabric having a basis weight of 20 g/m$^2$, which was formed by through-air bonding process from bicomponent synthetic fibers of PE and PET treated to be hydrophilic.

Absorbent layer 13: Mixture of crushed pulp having a basis weight of 400 g/m² and SAP (superabsorbent polymer) having a basis weight of 10 g/m².

First hydrophilic material layer 23: Fibrous web having a basis weight of 60 g/m² and a density of 0.05 g/cm³, which was formed by accumulating bicomponent synthetic fibers of PE and PP without fusion-bonding.

Second hydrophilic material layer 24: Fibrous web having a basis weight of 60 g/m² and a density of 0.009 g/cm³, which was similar to the fibrous web of the first hydrophilic material layer 23, except that the density was lowered.

Dimension

The entire length L0 was 300 mm, the entire length L1 of the raised region 20 was 180 mm, the length L2 of the front region 21 was 100 mm, the length L3 of the rear region 22 was 80 mm, the length L4 from the front edge 2 to the front end 27 of the raised region 20 was 50 mm, and the length L5 from the rear end 28 of the raised region 20 to the rear edge 3 was 70 mm.

The width W1 of the raised region 20 was 30 mm, the height H1 of the front region 21 of the raised region 20 was 5 mm, and the height H2 of the rear region 22 was 8 mm.

Comparative Examples (1) Comparative Example 1

Figure 6A:
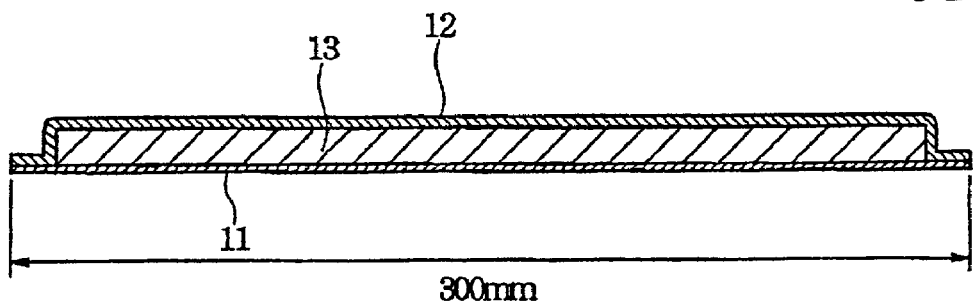
FIGS. 6A and 6B are sectional views of sanitary napkins for Comparative Examples.

As shown in FIG. 6A, a sanitary napkin having an entire length of 300 mm was prepared to have a structure similar to that of Example except with the first and second hydrophilic material layers 23 and 24 for forming the raised region removed.

(2) Comparative Example 2

Figure 6B:
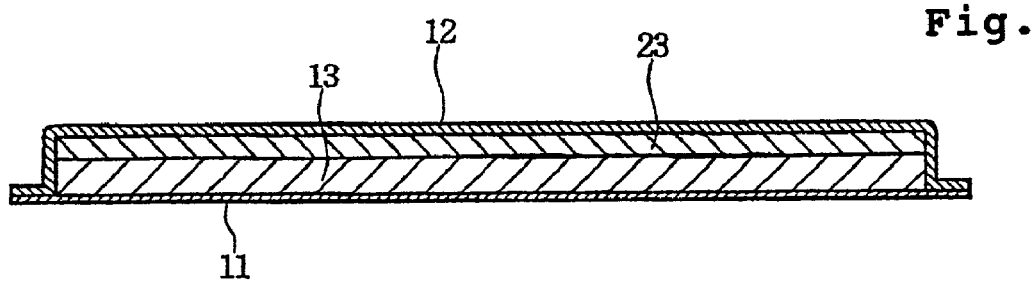

As shown in FIG. 6B, a sanitary napkin similar to that of Comparative Example 1 was prepared, except that a fibrous web formed by accumulating fibers similar to those of the first hydrophilic material layer 23 of Example was disposed over the entire surface of the absorbent layer 13. The fibrous web had a basis weight of 60 g/m² and a density of 0.05 g/cm³.

(3) Comparative Example 3

Figure 7A:
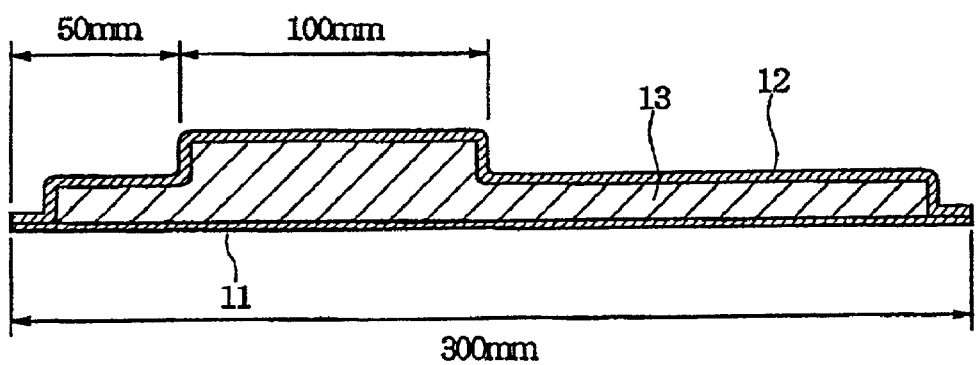
FIGS. 7A and 7B are sectional views of sanitary napkins for Comparative Examples.

As shown in FIG. 7A, a sanitary napkin similar to that of Comparative Example 1 was prepared, except that crushed pulp was disposed on the absorbent layer 13 at a basis weight of 300 g/m² to form a raised region having a length of 100 mm, rearwardly spaced apart from the front edge of the sanitary napkin by 50 mm. The raised region had a height of 8 mm and a width of 30 mm.

(4) Comparative Example 4

Figure 7B:
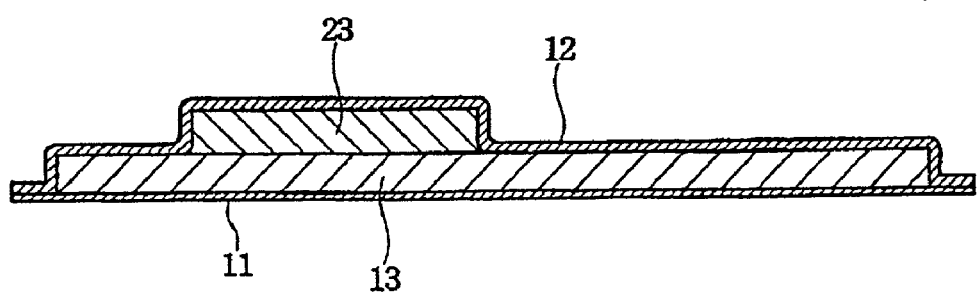

As shown in FIG. 7B, a sanitary napkin similar to that of Comparative Example 3 was prepared, except that a raised region having the same size as that of Comparative Example 3 was formed of a fibrous web having a basis weight of 60 g/m² similar to the first hydrophilic material layer 23 of Example.

(5) Comparative Example 5

Figure 8A:
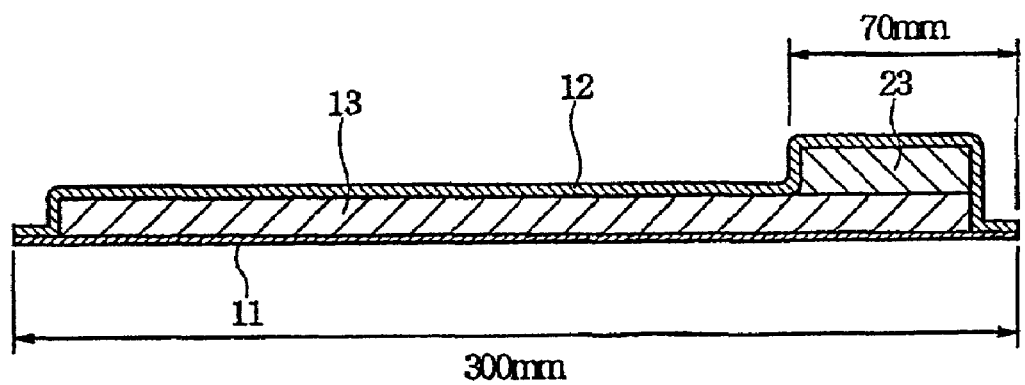
FIGS. 8A and 8B are sectional views of sanitary napkins for Comparative Examples.

As shown in FIG. 8A, a sanitary napkin similar to that of Comparative Example 1 shown in FIG. 6A was prepared, except that a fibrous web similar to the first hydrophilic material layer 23 of Example was disposed to form a raised region having a height of 8 mm, within a range of 70 mm from the rear edge of the sanitary napkin. The width of the raised region was set at 30 mm, and the basis weight of the fibrous web was set at 60 g/m².

(6) Comparative Example 6

Figure 8B:
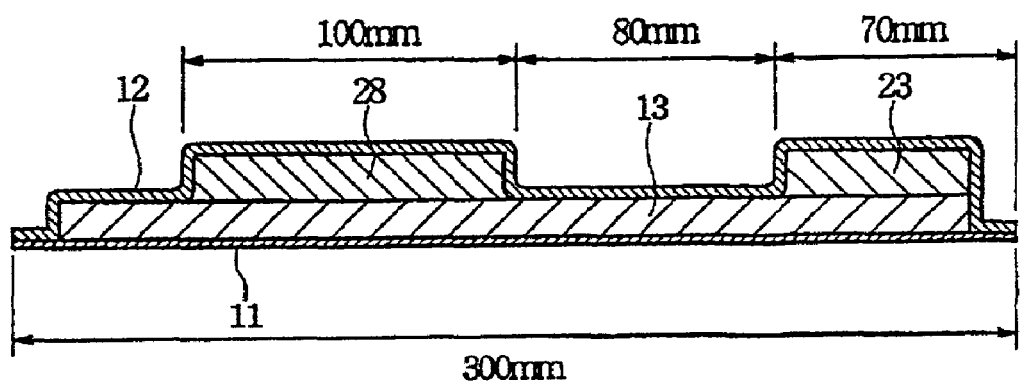

As shown in FIG. 8B, a sanitary napkin similar to that of Comparative Example 5 was prepared, except that another raised region having a length of 100 mm was formed, forwardly spaced apart from the front end of the raised region of Comparative Example 5 by 80 mm, to have the same width, height and basis weight as those of the raised region of Comparative Example 5.

<Comparison>

As areas to be measured, in the respective sanitary napkins of Example and Comparative Examples, the range having a length of 100 mm rearwardly from a start point spaced rearwardly apart from the front edge of the sanitary napkin by 50 mm (i.e., the area corresponding to the area of Example having the front region 21 of the length L2) was designated area A; and the range having a length of 80 mm rearwardly from a start point spaced rearwardly apart from the front edge of the sanitary napkin by 150 mm (i.e., the area corresponding to the area of Example having the rear region 22 of the length L3) was designated area B.

The amounts of the depressions were measured by applying a pressure of 3.43 kPa to the area A and area B, as set forth above. In addition, stiffnesses of the area A and area B were measured using the stiffness tester.

Furthermore, the sanitary napkins of Example and Comparative Examples were worn for 5 to 8 hours by 20 female monitors, respectively, to let them report how they felt on wearing.

Whether the napkin surface was certainly in close contact with the area from the vaginal opening to the gluteal fold or not was evaluated as fit. Comprehensive evaluation including such fit, a foreign body sensation, how the fit changed when the monitor's body moved, and so on was also carried out as availability.

when at least eight out of ten monitors reported that the sanitary napkin was preferable, it was indicated by "○"; when at least eight out of ten monitors reported that the sanitary napkin was not preferable, it was indicated by "X"; and the sanitary napkin which did not belong to either case was indicated by "Δ".

Results are shown in the following Table 1.

TABLE 1

| | Depression Amount upon Compression | | Stiffness | | | |
|---|---|---|---|---|---|---|
| | Area A (mm) | Area B (mm) | Area A (mN · m) | Area B (mN · m) | Fit | Availability |
| Example | 6 | 12 | 1.97 | 1.63 | ○ | ○ |
| Comp. Example 1 | 2 | 2 | 0.97 | 0.98 | X | ○ |
| Comp. Example 2 | 4 | 4 | 1.09 | 1.12 | X | ○ |
| Comp. Example 3 | 2 | 3 | 1.53 | 1.48 | X | X |
| Comp. Example 4 | 4 | 2 | 1.09 | 0.97 | Δ | ○ |

TABLE 1-continued

|  | Depression Amount upon Compression | | Stiffness | | | |
| --- | --- | --- | --- | --- | --- | --- |
|  | Area A (mm) | Area B (mm) | Area A (mN·m) | Area B (mN·m) | Fit | Availability |
| Comp. Example 5 | 2 | 2 | 0.98 | 0.96 | X | X |
| Comp. Example 6 | 4 | 2 | 1.11 | 0.99 | Δ | Δ |

As seen from the above comparison results, both the fit and the availability can be improved in the case where the amount of the depression of the area A upon compression is at least 3 mm, the amount of the depression of the area B upon compression is at least 5 mm, and the stiffnesses of the area A and area B are both at least 1.5 mN·m.

As has been described above, the sanitary napkin of the present invention can certainly fit against an area from the vaginal opening to the gluteal fold, thereby effectively preventing a menstrual blood discharged from the vaginal opening from leaking rearwardly out of the sanitary napkin.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. A sanitary napkin comprising:
   a backsheet;
   a liquid-permeable topsheet; and
   an absorbent layer for absorbing a liquid and disposed between the backsheet and the top sheet, at least a part of a region in which the absorbent layer is provided being adapted to act as a liquid-receiving region,
   wherein the liquid-receiving region includes:
      a raised region; and
      a peripheral region laterally provided around the raised region, the raised region being continuously elongated in the longitudinal direction of the sanitary napkin, the raised region including a front region for coming into contact with the vaginal opening of a wearer and a rear region for coming into contact with the buttocks of the wearer, the front region having a front hydrophilic material layer positioned between the liquid permeable topsheet and the absorbent layer, the rear region having a rear hydrophilic material layer positioned between the liquid permeable topsheet and the absorbent layer, the front hydrophilic material layer and the rear hydrophilic material layer causing the raised region to be higher than the peripheral region; and
   a compressed groove surrounding the raised region, the compressed groove being recessed from the surface of the peripheral region to create a depression between the raised region and the peripheral region,
   wherein when the front region and the rear region are respectively depressed with a given pressure applied to top surfaces of the front region and the rear region, an amount of depression of the top surface of the rear region in a direction orthogonal to the top surface of the rear region is larger than an amount of depression of the top surface of the front region in a direction orthogonal to the top surface of the front region.

2. The sanitary napkin as set forth in claim 1, wherein when the front region and the rear region are in a dry state and the top surfaces of the front region and the rear region are respectively depressed with a pressure of 3.43 kPa, the amount of the depression of the top surface of the front region is at least 3 mm and the amount of the depression of the top surface of the rear region is at least 5 mm.

3. The sanitary napkin as set forth in claim 1, wherein when an artificial body fluid is applied onto the front region and the rear region at the same amount and feed rate, an absorption speed of the artificial body fluid in the front region is faster than that in the rear region.

4. The sanitary napkin as set forth in claim 3, wherein when 3 cc of artificial body fluid is applied at a feed rate of 90 cc/minute, a difference in the absorption speed of the artificial body fluid between the front region and the rear region is in a range of 10 to 50 seconds.

5. The sanitary napkin as set forth in claim 3, wherein the absorption speed in the front region is equal to or less than 10 seconds, and the absorption speed in the rear region is equal to or less than 60 seconds.

6. The sanitary napkin as set forth in claim 1, wherein a height from the peripheral region to a surface of the rear region is larger than a height from the peripheral region to a surface of the front region.

7. The sanitary napkin as set forth in claim 6, wherein the height from the peripheral region to the surface of the rear region is at most 1.5 times the height from the peripheral region to the surface of the front region.

8. The sanitary napkin as set forth in claim 6, wherein both the height from the peripheral region to the surface of the front region and the height from the peripheral region to the surface of the rear region are in a range of 5 to 20 mm.

9. The sanitary napkin as set forth in claim 1, wherein a height from the peripheral region to a surface of the front region is equal to a height from the peripheral region to a surface of the rear region.

10. The sanitary napkin as set forth in claim 9, wherein both the height from the peripheral region to the surface of the front region and the height from the peripheral region to the surface of the rear region are in a range of 5 to 20 mm.

11. The sanitary napkin as set forth in claim 1, wherein the front region and the rear region of the raised region are identical in width, and a width of the raised region as measured at ½ of a height from the peripheral region to a surface of the raised region is in a range of 5 to 80 mm.

12. The sanitary napkin as set forth in claim 1, wherein when the respective front and rear regions are applied 10 cc of artificial body fluid at a feed rate of 10 cc/minute, allowed to stand for one minute after application of the artificial body fluid, and then applied a pressure of 3.43 kPa for one hour with a plates covering each top surface of the respective front and rear regions, bulk recovery percentages of the respective front and rear regions one minute later after removal of the pressure are equal to or more than 50%.

13. The sanitary napkin as set forth in claim 1, wherein when the sanitary napkin is in a dry state, a stiffness as measured by clamping front and rear ends of the raised region with a taper stiffness tester is in a range of 0.5 to 4.0 mN·m.

14. The sanitary napkin as set forth in claim 13, wherein when the sanitary napkin is in a dry state, a stiffness of the front region alone as measured with the taper stiffness tester is more than 1.0 times and less than or equal to 2.0 times a stiffness of the rear region alone as measured with the taper stiffness tester.

15. The sanitary napkin as set forth in claim 1, which further comprises leakage preventing walls disposed on both sides of the raised region and extending longitudinally of the sanitary napkin, rear ends of the leakage preventing walls being positioned closer to a rear end of the sanitary napkin than a rear end of the raised region.

16. The sanitary napkin as set forth in claim 1, wherein the front hydrophilic material layer has a higher density than the rear hydrophilic material layer.

17. A sanitary napkin comprising:
a backsheet;
a liquid-permeable topsheet; and
an absorbent layer disposed between the backsheet and the topsheet and having a liquid-receiving region;
a pair of walls disposed on top of the topsheet and laterally sandwiching the liquid-receiving region, wherein
the liquid-receiving region includes:
a raised region elongated in a longitudinal direction of the sanitary napkin and including a front region for coming into contact with the vaginal opening of a wearer and a rear region for coming into contact with the buttocks of the wearer; and
a peripheral region laterally provided around the raised region, which is raised higher than the peripheral region; and
a compressed groove surrounding the raised region and being recessed from the surface of the peripheral region to create a depression between the raised region and the peripheral region;
wherein rear ends of the pair of walls are positioned closer to a rear end of the sanitary napkin than a rear end of the raised region is positioned relative to the rear end of the sanitary napkin, and
wherein when the front region and the rear region are respectively depressed with a given pressure applied to top surfaces of the front region and the rear region, an amount of depression of the top surface of the rear region in a direction orthogonal to the top surface of the rear region is larger than an amount of depression of the top surface of the front region.

18. The sanitary napkin as set forth in claim 17, wherein a height from the peripheral region to a surface of the rear region is larger than a height from the peripheral region to a surface of the front region.

19. The sanitary napkin as set forth in claim 17, wherein a height from the peripheral region to a surface of the front region is equal to a height from the peripheral region to a surface of the rear region.

20. The sanitary napkin as set forth in claim 17, wherein the front region has a front hydrophilic material layer positioned between the liquid-permeable topsheet and the absorbent layer and the rear region has a rear hydrophilic material layer positioned between the liquid permeable topsheet and the absorbent layer.

21. The sanitary napkin as set forth in claim 20, wherein the front hydrophilic material layer has a higher density than the rear hydrophilic material layer.

* * * * *